(12) United States Patent
Okumura et al.

(10) Patent No.: US 9,447,066 B2
(45) Date of Patent: Sep. 20, 2016

(54) SALTS AND CRYSTAL FORMS

(71) Applicant: AskAt Inc., Aichi (JP)

(72) Inventors: Yoshiyuki Okumura, Aichi (JP); Yasuhiro Iwata, Aichi (JP); Toyoharu Numata, Aichi (JP); Masaki Sudo, Aichi (JP); Takako Okumura, Aichi (JP)

(73) Assignee: AskAt Inc., Aichi (JP)

( * ) Notice: Subject to any disclaimer, the term of this patent is extended or adjusted under 35 U.S.C. 154(b) by 0 days.

(21) Appl. No.: 14/655,175

(22) PCT Filed: Jan. 6, 2014

(86) PCT No.: PCT/JP2014/000010
§ 371 (c)(1),
(2) Date: Jun. 24, 2015

(87) PCT Pub. No.: WO2014/104414
PCT Pub. Date: Jul. 3, 2014

(65) Prior Publication Data
US 2015/0353520 A1 Dec. 10, 2015

Related U.S. Application Data

(60) Provisional application No. 61/746,945, filed on Dec. 28, 2012.

(51) Int. Cl.
*A61K 9/48* (2006.01)
*C07D 311/58* (2006.01)
*C07C 215/10* (2006.01)

(52) U.S. Cl.
CPC ........... *C07D 311/58* (2013.01); *A61K 9/4825* (2013.01); *C07C 215/10* (2013.01); *C07B 2200/13* (2013.01)

(58) Field of Classification Search
CPC ............ C07B 2200/13; C07D 311/58; A61K 9/4825
See application file for complete search history.

(56) References Cited

U.S. PATENT DOCUMENTS

| | | | |
|---|---|---|---|
| 6,034,256 A | 3/2000 | Carter et al. | |
| 6,077,850 A | 6/2000 | Carter et al. | |
| 6,271,253 B1 | 8/2001 | Carter et al. | |
| 6,590,709 B1 | 7/2003 | Ori et al. | |
| 6,649,645 B1 | 11/2003 | McKearn et al. | |
| 6,689,787 B1 | 2/2004 | McKearn et al. | |
| 6,806,288 B1 | 10/2004 | Carter et al. | |
| 6,833,373 B1 | 12/2004 | McKearn et al. | |
| 6,858,598 B1 | 2/2005 | McKearn et al. | |
| 2002/0010206 A1 | 1/2002 | Carter et al. | |
| 2002/0103141 A1 | 8/2002 | McKearn et al. | |
| 2003/0013739 A1 | 1/2003 | Masferrer | |
| 2003/0119895 A1 | 6/2003 | Masferrer et al. | |
| 2003/0153801 A1 | 8/2003 | Keller | |
| 2003/0203956 A1 | 10/2003 | Masferrer | |
| 2003/0225150 A1 | 12/2003 | Masferrer | |
| 2004/0038977 A1 | 2/2004 | Carter et al. | |
| 2004/0053900 A1 | 3/2004 | Masferrer | |
| 2004/0053934 A1 | 3/2004 | Masferrer | |
| 2004/0053935 A1 | 3/2004 | Masferrer | |
| 2004/0072889 A1 | 4/2004 | Masferrer | |
| 2004/0122011 A1 | 6/2004 | Masferrer et al. | |
| 2004/0127470 A1 | 7/2004 | Masferrer | |
| 2004/0127539 A1 | 7/2004 | Masferrer | |
| 2004/0234624 A1 | 11/2004 | McKearn et al. | |
| 2005/0037090 A1 | 2/2005 | McKearn et al. | |
| 2005/0049252 A1 | 3/2005 | Carter et al. | |
| 2005/0058725 A1 | 3/2005 | McKearn et al. | |
| 2006/0105961 A1 | 5/2006 | Masferrer | |
| 2006/0252766 A1 | 11/2006 | Masferrer et al. | |
| 2008/0194635 A1 | 8/2008 | Murtagh et al. | |
| 2009/0076120 A1 | 3/2009 | Takeyasu et al. | |

FOREIGN PATENT DOCUMENTS

| | | |
|---|---|---|
| CN | 1561246 A | 1/2005 |
| JP | 2002-511062 | 4/2002 |
| JP | 2006-199700 | 8/2006 |
| JP | 2008-534436 | 8/2008 |
| JP | 2008-542260 | 11/2008 |
| JP | 4577534 | 11/2010 |
| WO | 98/47890 | 10/1998 |
| WO | 2006/011047 | 2/2006 |
| WO | 2006/077497 | 7/2006 |
| WO | 2006/109836 | 10/2006 |
| WO | 2006/126214 | 11/2006 |
| WO | 2008/065502 | 6/2008 |

OTHER PUBLICATIONS

West, Anthony R., Solid State Chemistry and Its Applications, Wiley, New York, 1988, 358.*
International Search Report issued Mar. 25, 2014 in International (PCT) Application No. PCT/JP2014/000010.
Berge et al., "Pharmaceutical Salts", Journal of Pharmaceutical Sciences, vol. 66, No. 1, Jan. 1977, pp. 1-19.
Lokesh Kumar et al., "Salt Selection in Drug Development", Pharmaceutical Technology, vol. 32, No. 3, Mar. 2008, pp. 128-146.
Extended European Search Report issued Jun. 28, 2016 in corresponding European Patent Application No. 14733062.5.

* cited by examiner

Primary Examiner — Erich A Leeser
(74) Attorney, Agent, or Firm — Wenderoth, Lind & Ponack, L.L.P.

(57) ABSTRACT

This invention relates to salts and crystal forms of (S)-6-chloro-7-(1,1-dimethylethyl)-2-trifluoromethyl-2H-1-benzopyran-3-carboxylic acid, Compound A, which is cyclooxygenase-2 inhibitor. The present invention provides a salt of compound A, a crystal form thereof, a process for preparing the said salt and a pharmaceutical composition thereof and its use. The salts and/or co-crystals of Compound A of the present invention show good formulation properties such as high aqueous solubility, good intrinsic dissolution, good crystallinity, good thermal stability or low hygroscopicity.

11 Claims, 6 Drawing Sheets

Fig. 8
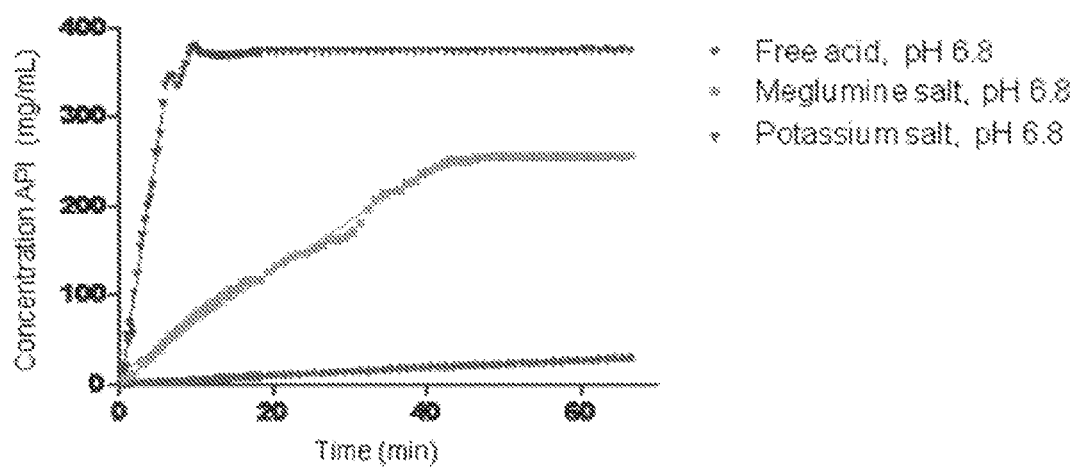
[Fig. 9]
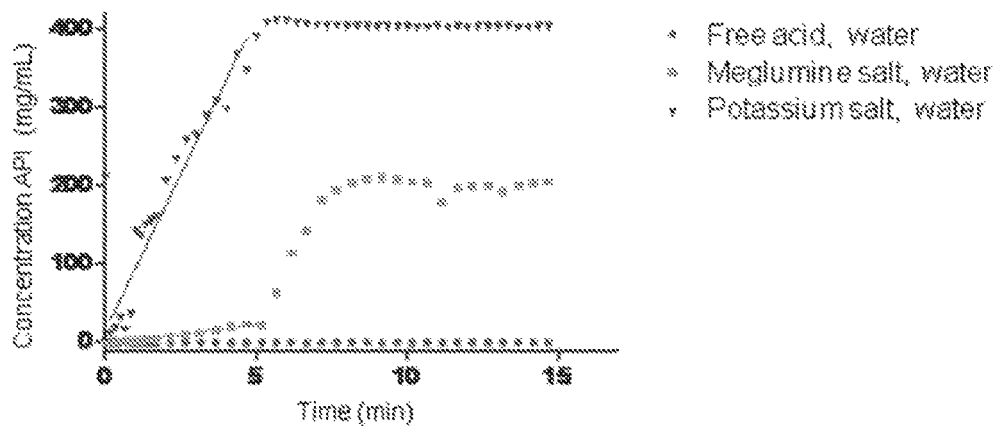

SALTS AND CRYSTAL FORMS

TECHNICAL FIELD

This invention relates to salts and crystal forms of (S)-6-chloro-7-(1,1-dimethylethyl)-2-trifluoromethyl-2H-1-benzopyran-3-carboxylic acid, which is cyclooxygenase-2 inhibitor, wherein the compound may be called Compound A through the present specification.

BACKGROUND ART

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, which limit their therapeutic potential. An alternative to NSAIDs is the use of corticosteroids, which have even more drastic side effects, especially when long term therapy is involved.

NSAIDs prevent the production of prostaglandins by inhibiting enzymes in the human arachidonic acid/prostaglandin pathway, including the enzyme cyclooxygenase (COX). The expression of cyclooxygenase-2 (COX-2) is specifically induced in the pathological conditions such as inflammation, pain, and cancer, and is involved in the generation and maintenance of these conditions. According to the line, a series of drugs called coxibs such as celecoxib, rofecoxib, valdecoxib, parecoxib, and etoricoxib have been developed.

Compound A is disclosed in the patent literature 1, and selectively inhibits cyclooxygenase-2 over cyclooxygenase-1. Compound A affords more potent analgesia, than ibuprofen which is the first choice among the conventional drugs. Furthermore it has been confirmed in the preclinical studies that Compound A has lower renal problem which are a matter of concern in conventional COX-2 inhibitors and NSAIDs.

Coxib-drugs are useful for the treatment of diseases mediated by cyclooxygenase-2, such as inflammation, pain, cancer, fever, osteoarthritis, rheumatoid arthritis, migraine, neurodegenerative diseases, cardiovascular disease, osteoporosis, asthma, lupus and psoriasis, dysmenorrhea, premature labor, glaucoma, gout, ankylosing spondylitis, bursitis, heat burn, sprain, and contusion.

In general, active ingredients involved in coxib-drugs have a sulfonamide group, whereas Compound A is a unique chemical structure, which has neither sulfonamide group nor alkylsulfonyl group but has a carboxylic acid group. Hereafter in the present specification, such coxib-drugs or coxib-compounds, which have neither a sulfonamide group nor an alkylsulfonyl group but have a carboxylic acid group, are called third generation coxib-drugs or third generation coxib-compounds. As Compound A has a carboxylic acid group in its chemical structure, the solubility in the low pH field is inferior to that in the neutral or basic condition. Therefore, depending on gastric residence time, the solubility problem may cause the precipitation of the compound followed by insufficient absorption, resulting in decreasing blood concentration and bioavailability. These adverse events are observed in common with third generation coxib-drugs or third generation coxib-compounds defined in the present specification.

Actually, results of clinical studies are obtained that when Compound A through the present specification, was administered with the standard tablet formulation, the initial blood concentration after the administration was low comparing with administered with the solution (OPC, Oral Powder Constitution: a solution in which the active ingredient is simply dissolved).

From this background, it has been investigated that a method for providing a pharmaceutical composition of a cyclooxygenase-2 inhibitor in which the stability and/or solubility are improved. Namely, the patent literature 2 discloses "a novel injectable pharmaceutical composition comprising at least one COX-2 inhibitor or NSAID or COX/LOX inhibitor or its tautomeric forms, or its analogues, isomers, polymorphs, solvates, prodrugs, or salts or thereof as active ingredient from 0.1% to 80% w/v and a solvent system comprising a mixture of glycols from 1% to 80% v/v; optionally with other pharmaceutically acceptable excipients" and also discloses "a composition according to claim 1, wherein the said composition additionally comprises at least one alkalizing agent from 0.2% to 60% v/v". However, this is a pharmaceutical formulation as an injectable drug, and therefore an effectual means as an oral formulation which solves these issues has been desired. In addition, other technologies for solving such issues have also been desired.

As a method for keeping the basicity of the third generation coxib-drugs, a method of adding a base such as calcium carbonate, calcium hydroxide, magnesium carbonate, magnesium silicate, and magnesium aluminate as an excipient was tried, but when adding such a basic alkaline-earth metal salt to Compound A, no preferable results were obtained.

CITATION LIST

Patent Literature

{PL 1} JP Patent No. 4577534
{PL 2} Japanese Unexamined Patent Application Publication (Translation of PCT Application) No. 2008-542260 pamphlet

SUMMARY OF INVENTION

Problems to be Resolved by the Invention

It is an object of the present invention to provide a salt of Compound A, a crystal form thereof and a pharmaceutical composition containing the salt which exerts with good formulation properties while avoiding the aforementioned disadvantages. It is also an object to provide a process for preparing the said salt and a pharmaceutical composition thereof and its use.

Means for Solving the Problem

Taking the above circumstances into consideration, after an exhaustive and careful study aiming to identify salts and/or co-crystals of Compound A with good formulation properties such as high aqueous solubility, good crystallinity, good thermal stability or low hygroscopicity, surprisingly the inventors of the present invention have managed to find out the meglumine salt and the potassium salt. The present invention also provides a crystal form thereof, process for preparing the said salt and a pharmaceutical composition thereof and its use.

Various counter bases against Compound A as an excipient were tried, no preferable results were obtained. Examples of counter bases include sodium hydroxide, calcium carbonate, calcium hydroxide, magnesium carbonate, magnesium silicate, magnesium aluminate as mentioned in the background art. In addition, ammonia, L-arginine, benzathine, betaine, calcium hydroxide, choline hydroxide, diethyl amine, nicotinamide, L-tartaric acid, and the like were neither suitable for the salt formation nor suitable for formulation.

In the present invention, two Compound A salts, the meglumine salt and the potassium salt have much more suitable for formulation than any other salt in terms of crystallization of the selected salts, manufacturability related studies (stability under variable temperature and humidity, slurry experiments) or bioavailability related studies (solubility and dissolution rate).

Meglumine Salt

The meglumine salt was readily obtained from the crystallization experiments in ethanol and isopropanol. The solids precipitated right after addition of the solvents. All performed stability tests, under variable temperature and humidity XRPD experiments as well as the slurry experiments, showed that the meglumine salt is stable, both physically and chemically while its chiral purity remained practically unchanged. Therefore, from the manufacturing point of view, the meglumine salt is a very suitable candidate salt and performed the best amongst the tested salts.

From the solubility/dissolution rate point of view, the meglumine salt of Compound A has higher solubility and faster dissolution rates compared to the free acid of Compound A. Therefore, from the aspect of the solubility/dissolution rate, the meglumine salt is suitable for an active pharmaceutical ingredient of a pharmaceutical composition of Compound A. By using the meglumine salt, bioavailability of Compound A is improved. The present invention is based on the above unexpected and surprising findings. In addition, compared to the case where free carboxylic acid of Compound A was administered, in the case where meglumine salt was administered, more rapid onset of effect and long duration of action are observed in the dog-Pharmacokinetic studies as shown in FIG. 10.

Potassium Salt

The potassium salt of Compound A was obtained from aqueous solvent mixtures. Although it is not difficult to obtain a potassium salt of Compound A, it is difficult to obtain a stable and single crystal form of the potassium salt because, in crystallization process, the water content in solvent mixtures sensitively influences to the formation of the crystal. Therefore, the control of water content is essential for obtaining the stable and single crystal form, and excess water must be removed under azeotropic condition with suitable solvent, such as toluene, ethyl acetate, and ethanol. The water content is 1 to 1.5 molar equivalent against the free acid, preferably, the water content is 1 to 1.2 molar equivalent, more preferably the water content is 1 to 1.1 molar equivalent, the most preferably the water content is 1 to 1.05 molar equivalent. If the water content is more than 1.5 molar equivalent against the free acid, target single crystal form is never obtained. The potassium salt showed good stability both chemically and enantiomerically after the solid-state stability experiments.

The solubility of the potassium salt is more than 120 mg/mL in a neutral to basic environment. In the dissolution rate, the potassium salt was completely dissolved in the neutral media within 15 min, especially dissolved in water within 5 min, while Compound A free acid showed very limited dissolution. The present invention is based on the above unexpected and surprising findings. In addition, compared to the case where free carboxylic acid of Compound A was administered, in the case where potassium salt was administered, comparing meglumine salt with free carboxylic acid, more rapid onset of effect, long duration of action and improved bioavailability have been observed in the dog-Pharmacokinetic studies as shown in FIG. 10.

More specifically, this invention discloses:

[1] A salt of (S)-6-chloro-7-(1,1-dimethylethyl)-2-trifluoromethyl-2H-1-benzopyran-3-carboxylic acid; wherein the salt is selected from the group consisting of the meglumine salt and the potassium salt;

[2] The salt according to [1], wherein the potassium salt is hydrate;

[3] The salt according to [1], wherein the potassium salt is monohydrate;

[4] A Crystal form of the meglumine salt according to [1], which is characterized by a powder X-ray diffraction pattern (PXRD) obtained by irradiation with Cu—K$\alpha$ radiation which includes main peaks at 2-Theta 4.6, 8.9, 10.1, 13.8, 16.0, 16.7, 17.3, 18.0, 19.5, 22.4 and 23.2 (°), and each peak has a margin of error of +/−0.2 (°);

[5] A Crystal form of the potassium salt according to any one of [1] to [3], which is characterized by a powder X-ray diffraction pattern (PXRD) obtained by irradiation with Cu—K$\alpha$ radiation which includes main peaks at 2-Theta 3.8, 11.4, 12.7, 14.7, 15.8, 16.5, 17.4, 18.9, 19.5 and 21.8 (°), and each peak has a margin of error of +/−0.2 (°);

[6] A pharmaceutical composition which comprises a pharmaceutically acceptable carrier and an amount of the salt as defined in any one of [1] to [5];

[7] A process for preparing a pharmaceutical composition, wherein the process comprises a step for combining the salt as defined in any one of [1] to [5] and a pharmaceutically acceptable carrier;

[8] The process for preparing a pharmaceutical composition according to [7], wherein the process comprises combining the salt as defined in any one of [1] to [5] and at least one carrier; and subjecting the combination to grinding or milling, sieving, blending, drying, or granulation;

[9] The process according to [7] or [8], wherein the process further comprises compressing the pharmaceutical composition into a solid dosage form;

[10] The process for preparing a potassium salt as defined in any one of [1], [3], [4] and [5], wherein the process comprises lower than 1.5 molar equivalent of water content in solvent mixture of crystallization against the free (S)-6-chloro-7-(1,1-dimethylethyl)-2-trifluoromethyl-2H-1-benzopyran-3-carboxylic acid;

[11] The process according to [10], wherein the water content is selected from the group consisting of a) 1 to 1.5, b) 1 to 1.2, c) 1 to 1.1 and d) 1 to 1.05;

[12] A use of a pharmaceutical composition, as defined in [6] for the manufacture of a medicament for treating and/or preventing a patient suffering from a disease mediated by cyclooxygenase-2; and

[13] The use according to [12], wherein the disease is one or more diseases selected from the group consisting of inflammation, pain, cancer, fever, osteoarthritis, rheumatoid arthritis, migraine, neurodegenerative diseases, cardiovascular diseases, osteoporosis, asthma, lupus and psoriasis, dysmenorrhea, premature labor, glaucoma, gout, ankylosing spondylitis, bursitis, heat burn, sprain, and contusion.

Effect of the Invention

The present invention provides a salt of compound A, a polymorph form thereof, a process for preparing the said salt and a pharmaceutical composition thereof and its use. The salts and/or co-crystals of Compound A of the present invention show good formulation properties such as high aqueous solubility, good crystallinity, good thermal stability or low hygroscopicity.

BRIEF DESCRIPTION OF DRAWINGS

FIG. 8 shows the concentrations vs. time of all solids measured in the pH 6.8 buffer.

FIG. 9 shows the concentrations vs. time of all solids measured in water.

DETAILED DESCRIPTION OF THE INVENTION

Compound A

Figure 1:
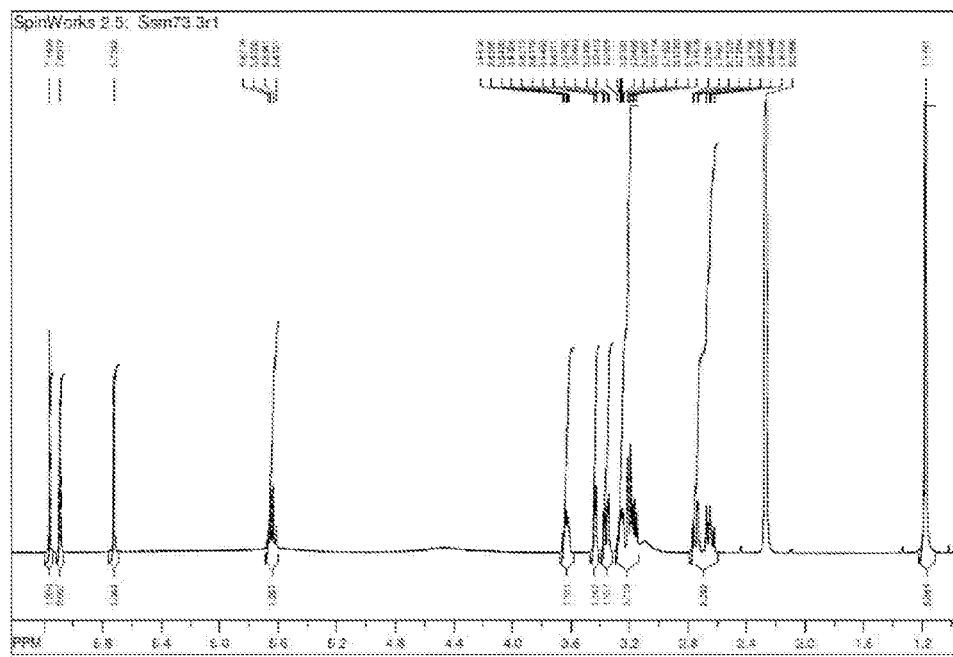
FIG. 1 shows the NMR spectrum of (S)-6-chloro-7-(1,1-dimethylethyl)-2-trifluoromethyl-2H-1-benzopyran-3-carboxylic acid meglumine salt.

Compound A can be prepared by a method known per se.
For example, Compound A is described in the patent literature 1, JP Patent No. 4577534, etc.

The amount of the salt of the present invention contained in a pharmaceutical composition for treating circulatory system diseases according to the present invention is not specifically restricted, however, the dose preferably should be sufficient to treat, ameliorate, or reduce the symptoms associated with the circulatory system disease. The dosage of a pharmaceutical composition for treating circulatory system diseases according to the present invention will depend on the method of use, the age, sex, and condition of the patient. For example, about 1 mg to 1000 mg of the salt of the present invention may be contained in a dosage form. Preferably, about 5 mg to 500 mg of the salt of the present invention may be contained there.

(The Process for Preparing a Pharmaceutical Composition)

The pharmaceutical composition of the present invention may be prepared by any conventional means such as, but not limited to, wet or dry granulation and direct compression.

The process for preparing the pharmaceutical composition of the present invention is characterized by containing a process for combining the meglumine, or the potassium hydroxide with an active pharmaceutical ingredient, Compound A.

In a direct compression process, the process for preparing a pharmaceutical composition comprises combining a salt of the present invention and at least one carrier, wherein the carrier is intimately admixed with a salt of the present invention. Optionally, one or more other excipients are added to the pharmaceutical composition and the resulting combination is compressed into a solid pharmaceutical composition such as tablets, pills, granules, etc. Preferably, the solid pharmaceutical composition is compressed into a tablet.

In a similar way to the direct compression process, a wet granulation process comprises adding and kneading an appropriate amount of water to the pharmaceutical composition to be formulated and through a further suitable process. The granulated pharmaceutical composition is dried under a suitable condition, and is subject to compression molding to tablet etc after particle size regulation.

Then in a similar way to the direct compression process, a dry granulation process comprises compression molding which comprises compressing a pharmaceutical composition to be formulated to the form of plates with a suitable compressor, crushing the resulting plate with a grinder mill, successively regulating a particle size, and then compression molding to tablet etc.

The agents such as sodium hydroxide, potassium hydroxide, calcium carbonate, calcium hydroxide, magnesium carbonate, magnesium silicate, magnesium aluminate, ammonia, L-arginine, benzathine, betaine, calcium hydroxide, choline hydroxide, diethyl amine, potassium hydroxide, meglumine, nicotinamide, and L-tartaric acid, which are used in the present specification are commercially available.

The salt of this invention may be used alone or in a combination of one or two or more kinds of salts of Compound A thereof. The agent of meglumine or potassium hydroxide is added in the form of liquid, solid, or suspensions.

In the oral pharmaceutical composition of the present invention, the salt of this invention is generally ranged from about 1 to 60% (w/w) in the said composition.

The pharmaceutical composition of the invention may take any form but it is preferably a solid composition. More preferably, the pharmaceutical composition of the invention is compressed to solid composition by molding (e.g. granulation and pressurization). Suitable solid dosage forms include, but are not limited to, tablets, pill, granules, capsules, powders, and sachets, and the like. Particularly tablets are preferable.

When the pharmaceutical composition is a solid dosage form, the dosage form can be produced by incorporating the salt of the present invention, followed by subjecting the mixture to molding. The incorporation is conducted by a method conventionally employed in the field of pharmaceutical preparations, such as mixing, kneading, massing, sieving, stirring and the like. For example, a pharmaceutically acceptable carrier may be directly mixed with the salt of the present invention (addition in a powder state), or a solvent may be added to the mixture, followed by conventional kneading, granulating and drying. Alternatively, a carrier is dissolved in a suitable solvent, then the solution is uniformly mixed with the active ingredient, followed by conventional kneading, granulating and drying (addition in a liquid state). In the case of addition in a liquid state, any solvent which does not exert undesirable influence on the active ingredient, for example, water, dimethylformamide, acetone, ethanol, propyl alcohol, isopropyl alcohol, butyl alcohol, methylene chloride, trichloroethane etc., can be employed. After completion of blending, the material is subjected to a conventional molding process under pressurization to prepare tablets containing the active ingredient. The molding under pressurization means that a material is compressed under pressurization into a desired form, which most generally refers to tableting.

It is also possible to add a variety of carriers to be employed for preparation making to the solid pharmaceutical composition (e.g. solid preparations) of the present invention in an adequate step. Examples include, but not limited to, fillers, diluents, disintegrants, glidants, excipients, binders, lubricants, colorant, flavoring agents, odor-improving agents, wetting agents, and the like.

Suitable fillers and diluents include, but are not limited to, cellulose-derived materials like powdered cellulose, microcrystalline cellulose (e.g. Avicel (registered trademark)), microfine cellulose, methyl cellulose, ethyl cellulose, hydroxyethyl cellulose, hydroxypropylcellulose, hydroxypropylmethylcellulose, carboxymethylcellulose salts and other substituted and unsubstituted celluloses; starch; pregelatinized starch; lactose; talc; waxes; sugars; sugar alcohols like mannitol and sorbitol; acrylate polymers and copolymers; dextrates; dextrin; dextrose; maltodextrin; pectin; gelatin; inorganic diluents like calcium carbonate, dibasic calcium phosphate dihydrate, tribasic calcium phosphate, magnesium carbonate, magnesium oxide, sodium chloride and other diluents known to the pharmaceutical industry.

Suitable disintegrants include, but are not limited to, croscarmellose sodium (e.g. Ac Di Sol (registered trademark), Primellose (registered trademark)), crospovidone (e.g. Kollidon (registered trademark), Polyplasdone (registered trademark)), microcrystalline cellulose, polacrilin potassium, powdered cellulose, pregelatinized starch, sodium starch glycolate (e.g. Explotab (registered trademark), Primoljel (registered trademark)) and starch, and the like.

Glidants can be added to improve the flowability of a solid composition before compaction and to improve the accuracy of dosing especially during compaction and capsule filling. Excipients that may function as glidants include, but are not limited to, colloidal silicon dioxide, magnesium trisilicate, powdered cellulose, talc, and the like.

Suitable excipients that may be incorporated into the formulation include, but are not limited to, microcrystalline cellulose (for example, Avicel PH101, PH101 (manufactured by Asahi Kasei Corporation)), carboxymethylcellulose calcium, corn starch, wheat starch, lactose, sucrose, glucose, calcium sulfate, calcium phosphate, sodium chloride, and so on. In addition, such excipients include preservatives, surfactants, antioxidants, or any other excipient commonly used in the pharmaceutical industry.

Suitable binders that may be incorporated into the formulation include, but are not limited to, water, ethanol, propanol, simple syrup, glucose solutions, starch solutions, gelatin solutions, gum arabic, gelatin, sodium alginate, methyl cellulose, carboxymethylcellulose, shelac, polyvinylpyrrolidone, crospovidone, hydroxypropylcellulose (which may be hereinafter referred to as HPC), hydroxypropylmethylcellulose, and the like. In addition, such binders include other binders used in wet or dry granulation and in direct compression tableting processes.

Suitable lubricants that may be incorporated into the formulation include, but are not limited to, magnesium stearate, talc, synthetic aluminum silicate, sodium lauryl sulfate, boric acid, magnesium oxide, paraffin, and the like. In addition, colorant, flavoring agents, odor-improving agents, wetting agents, and the like may be added.

Incidentally, in the case of using a crystalline compound whose specific gravity is relatively small as an active pharmaceutical ingredient, it is desirable to have the compound dispersed in advance in a thick liquid containing such a binder as HPC and water. Furthermore, the solid pharmaceutical composition of the present invention can be prepared into coated tablets as well.

The coating may be conducted by a method known per se. As the coating agents, conventional coating agents (e.g. hydroxypropylmethylcellulose, hydroxypropylcellulose, methylcellulose, polyvinylpyrrolidone etc.), and as auxiliary agents for coating, use is made of, for example, polyethylene glycol 6000, polysorbate (e.g. Tween 80 etc.), titanium oxide, and pigments such as red iron oxide or the like.

In the case of using the pharmaceutical composition of this invention for the treatment of diseases mediated by cyclooxygenase-2 in animals (e.g. man, dog, rabbit or rat), it can be administered orally as tablets, etc. The dosage ranges from 0.0075 to 15 mgA/kg per day, preferably from 0.07 to 7.2 mgA/kg per day in terms of the active pharmaceutical ingredient (wherein mgA means mg weight of the active pharmaceutical ingredient based on the free acid). The dosage can be increased or decreased depending on the disease or condition.

Compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention is envisioned. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly.

Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is envisioned. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, including about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The salt or crystal forms thereof, as defined above, may be administered simultaneously, sequentially or separately in combination with one or more agents selected from an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an H1 antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex (registered trademark), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2 (1H)-quinolinone;

an alpha-adrenergic, e.g. doxazosin, tamsulosin, clonidine, guanfacine, dexmedetomidine, modafinil, or 4-amino-6,7-dimethoxy-2-(5-methane-sulfonamido-1, 2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g. oxybutynin, tolterodine, propiverine, trospium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion (registered trademark) or sarizotan;

a vanilloid receptor agonist (e.g. resiniferatoxin) or antagonist (e.g. capsazepine);

a transient receptor potential cation channel subtype (V1, V2, V3, V4, M8, M2, A1) agonist or antagonist;

a beta-adrenergic such as propranolol;

a local anaesthetic such as mexiletine;

a corticosteroid such as dexamethasone;

a 5-HT receptor agonist or antagonist, particularly a 5-HT1B/1D agonist such as eletriptan, sumatriptan, naratriptan, zolmitriptan or rizatriptan;

a 5-HT2A receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol (registered trademark);

a PDEV inhibitor, such as 5-[2-ethoxy-5-(4-methyl-1-piperazinylsulphonyl)phenyl]-1-methyl-3-n-propyl-1, 6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)pyrazino[2',1':6,1] pyrido[3,4-b]indole-1,4-dione (IC-351 or tadalafil), 2-[2-ethoxy-5-(4-ethyl-piperazin-1-yl-sulphonyl)phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (3-(aminomethyl)-bicyclo[3.2.0]hept-3-yl)acetic acid, (3S,5R)-3-(aminomethyl)-5-methylheptanoic acid, (3S,5R)-3-amino-5-methylheptanoic acid, (3S,5R)-3-amino-5-methyloctanoic acid, (2S,4S)-4-(3-chlorophenoxy)proline, (2S,4S)-4-(3-fluorobenzyl)proline, [(1R,5R,6S)-6-(aminomethyl)bicyclo[3.2.0]hept-6-yl]acetic acid, 3-((1-(aminomethyl)cyclohexyl)methyl)-4H-[1,2,4]oxadiazol-5-one, C[1-((1H-tetrazol-5-yl)methyl)cycloheptyl]methylamine, (3S,4S)-(1-(aminomethyl)-3,4-dimethylcyclopentyl) acetic acid, (3S,5R)-3-(aminomethyl)-5-methyloctanoic acid, (3S,5R)-3-amino-5-methylnonanoic acid, (3S,5R)-3-amino-5-methyloctanoic acid, (3R,4R,5R)-3-amino-4,5-dimethylheptanoic acid, and (3R,4R,5R)-3-amino-4,5-dimethyloctanoic acid;

a cannabinoid;

a metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazapine, oxaprotiline, fezolamine, tomoxetine, mianserin, buproprion, buproprion metabolite hydroxybuproprion, nomifensine and viloxazine (Vivalan (registered trademark)), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S[2-[(1-iminoethyl)amino]ethyl]-L-homocysteine, S[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy]pyridin-3-yl]carbonyl}amino)ethyl]benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-meth yl-2-quinolone (ZD-2138), or 2,3,5-trimethyl-6-(3-pyridylmethyl),1,4-benzoquinone (CV-6504);

a sodium channel blocker, such as lidocaine;

a calcium channel blocker, such as ziconotide, zonisamide, mibefradil;

a 5-HT3 antagonist, such as ondansetron;

a chemotherapy drug such as oxaliplatin, 5-fluorouracil, leukovolin, paclitaxel;

a calcitonin gene related peptide (CGRP) antagonist;

a bradykinin (BK1 and BK2) antagonist;

a voltage gated sodium dependent channel blocker ($Na_{v1.3}$, $Na_{v1.7}$, $Na_{v1.8}$);

a voltage dependent calcium channel blocker (N-type, T-type);

a P2X (ion channel type ATP receptor) antagonist;

an acid-sensing ion channel (ASIC1a, ASIC3) antagonist;

an Angiotensin AT2 antagonist;

a Chemokine CCR2B receptor antagonist;

a Cathepsin (B, S, K) inhibitor;

a signal receptor agonist or antagonist;

and the pharmaceutically acceptable salts and solvates thereof.

Such combinations offer significant advantages, including synergistic activity, in therapy.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred. Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or *acacia*), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound or pharmaceutically acceptable salt thereof.

For parenteral administration, fluid unit dosage forms are prepared utilising a salt of Compound A of the present invention or a crystal form thereof and a sterile vehicle. Formulations for injection may be presented in unit dosage form e.g. in ampoules or in multi-dose, utilising a salt of Compound A of the present invention or a crystal form thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

A salt of Compound A of the present invention or a crystal form thereof may also be formulated in rectal compositions such as suppositories or retention enemas, e.g. containing conventional suppository bases such as cocoa butter or other glycerides.

A salt of Compound A of the present invention or a crystal form thereof may also be formulated as depot preparations. Such long acting formulations may be administered by implantation (for example subcutaneously or intramuscularly) or by intramuscular injection. Thus, for example, a salt of Compound A of the present invention or a crystal form thereof may be formulated with suitable polymeric or hydrophobic materials (for example as an emulsion in an acceptable oil) or ion exchange resins, or as sparingly soluble derivatives, for example, as a sparingly soluble salt.

For intranasal administration, a salt of Compound A of the present invention or a crystal form thereof may be formulated as solutions for administration via a suitable metered or unitary dose device or alternatively as a powder mix with a suitable carrier for administration using a suitable delivery device. A salt of Compound A of the present invention or a crystal form thereof may be formulated for oral, buccal, parenteral, topical (including ophthalmic and nasal), depot or rectal administration or in a form suitable for administration by inhalation or insufflation (either through the mouth or nose). A salt of Compound A of the present invention or a crystal form thereof may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilized components.

When the pharmaceutical composition is in the dosage form of a capsule, the capsule may contain the pharmaceutical composition of the invention in a form of uncompressed or compressed granulates or powder mixes, etc. The capsules may be covered with either a hard shell or a soft shell. The shells may be made from, but not limited to gelatin and optionally contain a plasticizer such as glycerin and sorbitol, and an opacifying agent or colorant.

Methods of administration of a pharmaceutical composition for treating diseases mediated by cyclooxygenase-2 in the present invention are not specifically restricted, and can be administered in various preparations depending on the age, sex, and symptoms of the patient. Suitable routes for administrating a pharmaceutical composition may include, but not limited to, oral, buccal, and rectal administration. Although the most suitable administration in any given case will depend on the nature and severity of the condition being treated, the most preferred route of administration of the present invention is oral. The dosages may be conveniently presented in unit dosage form and prepared by any of the methods commonly known in the pharmaceutical art.

Having described the invention with reference to certain preferred embodiments, other embodiments will become apparent to those skilled in the art from consideration of the specification. The invention is further explained by reference to the following examples, but they are just examples, which never limit the present invention. It will be apparent to those skilled in the art that many modifications, both to materials and methods, may be practiced without departing from the scope of the invention.

EXAMPLES

The present invention is explained in more detail in the following by referring to Reference Examples and Examples, which are not to be construed as limitative but just typical examples.

Compound A can be prepared using any method known in the art (for example, patent literature 1, JP Patent No. 4577534).

DEFINITIONS AND ABBREVIATIONS

Solvent and Counter-Ion Abbreviations

AcN: Acetonitrile
EtOH: Ethanol
EtOAc: Ethyl acetate
IPA: Isopropanol
MeOH: Methanol
2-MeTHF: 2-Methyltetrahydrofuran
MTBE: Methyl tert-butyl ether
TFA: Tri-fluoroacetic acid Other Abbreviations (Alphabetical Order)

API: Active Pharmaceutical Ingredient, i.e. (S)-6-chloro-7-(1,1-dimethylethyl)-2-trifluoromethyl-2H-1-benzopyran-3-carboxylic acid
DSC: Differential Scanning calorimetry
FTIR: Fourier Transform Infrared spectroscopy
HPLC: High-Performance Liquid Chromatography
LCMS: Liquid Chromatography coupled with Mass Spectroscopy
MS: Mass Spectroscopy
RH: Relative Humidity
XRPD: X-Ray Powder Diffraction
Analysis 1. X-Ray Powder Diffraction XRPD patterns were obtained using the Crystallics T2 high-throughput XRPD set-up. The plates were mounted on a Bruker GADDS diffractometer equipped with a Hi-Star area detector. The XRPD platform was calibrated using Silver Behenate for the long d-spacings and Corundum for the short d-spacings.

Data collection was carried out at room temperature using monochromatic Cu—Kα (alpha) radiation in the 2θ region between 1.5° and 41.5°, which is the most distinctive part of the XRPD pattern. The diffraction pattern of each well was collected in two 2θ ranges (1.5°≤2θ≤21.5° for the first frame, and 19.5°≤2θ≤41.5° for the second) with an exposure time of 90 s for each frame. No background subtraction or curve smoothing was applied to the XRPD patterns. The carrier material used during XRPD analysis was transparent to X-rays and contributed only slightly to the background.

2. High-Resolution X-Ray Powder Diffraction:

The High-Resolution X-ray powder diffraction patterns were collected on the D8 Advance system in the Brag-Brentano geometry equipped with LynxEye solid state detector. The radiation used for collecting the data was Cu—Kα1 (λ=1.54056 Å) monochromatized by germanium crystal. The patterns were collected in the range of 4 to 41.5° 2θ, with a step in the range of 0.016° 2θ without further processing. All patterns were taken at Room Temperature, approximately 295K. The material was placed in a boron glass capillary of 0.3 mm diameter.

For variable humidity and temperature experiment the ANSYCO HT chamber was used. The material was placed on a fixed sample holder that was mounted inside the chamber. The humidity was applied locally and varied from 10 to 80% (dew point). The temperature variation rate was 10° C./min.

3. Thermal Analysis

Melting properties were obtained from DSC thermograms, recorded with a heat flux DSC822e instrument (Mettler-Toledo GmbH, Switzerland). The DSC822e was calibrated for temperature and enthalpy with a small piece of indium (m.p.=156.6° C.; ΔHf=28.45 J·g−1). Samples were sealed in standard 40 µl aluminium pans, pin-holed and heated in the DSC from 25° C. to 300° C., at a heating rate of 10° C. min$^{-1}$. Dry N$_2$ gas, at a flow rate of 50 ml min was used to purge the DSC equipment during measurement.

4. DVS Analysis

Moisture sorption isotherms of small samples were obtained using a DVS-1 system from Surface Measurement Systems (London, UK) with an accuracy of 0.1 µg. The relative humidity cycled between 45 and 95% RH (sorption), 95 to 0% RH (desorption) and 0 to 45% (sorption) at a constant temperature of 25° C. with a hold time of 60 minutes per step (10% relative humidity step). At the end of the DVS experiment the sample was measured by XRPD.

5. FTIR

The FTIR spectra were recorded on a ThermoFischer Scientific FT-IR: Nicolet 6700. Reported values are rounded and should therefore be considered approximate.

6. NMR $^1$H NMR spectroscopy in DMSO-d$_6$ was used for compound integrity characterization. The spectra were recorded at room temperature on a 500 MHz instrument using standard pulse sequences unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc.

7. HPLC Analytical Method

Chemical purity is obtained by Agilent 1200 system with Agilent 1100 API-ES MSD VL-type using the following conditions;
Column: Waters Sunfire C18 (100×4.6 mm; 3.5 µm),
Eluent: 0.1% TFA/AcN=35/65-5/95
UV detection: 235 nm,
MS detection: positive
Flow rate: 1 mL/min, and
Column temperature: 40° C.
Chiral purity is obtained by Agilent 1200 system using the following conditions;
Column: Chiralpak AD-RH (4.6 mm×150 mm 5 um),
Eluent: EtOH/H2O/Ethanesulfonic Acid=80/20/0.1
Detection: 235 nm,
Flow rate: 0.5 mL/min, and
Column temperature: 40° C.

Example 1

The API (253 mg) and meglumine (166 mg) were weighed into 8 ml vial. Then isopropanol (5 ml) was added. The mixture was hazy, and precipitation occurred within a few minutes. The slurry was left under stirring for 17 hours. Subsequently, the solids were separated from the liquids by centrifugation. The liquid was removed with a pipette and the solids were dried under vacuum for 24 hours. 500 µl of water were added to the solids. The mixture was shaken for 5 minutes. The solids were separated from the solvent after centrifugation and removal of water with a pipette, and they were dried under vacuum for 24 hours to provide the meglumine salt (404 mg, 96% yield).

NMR (FIG. 1): $^1$H-NMR (DMSO-d$_6$) delta: 7.16 (s, 1H), 7.09 (s, 1H), 6.72 (s, 1H), 5.64 (q, J=7.5 Hz, 1H), 3.66-3.60 (m, 1H), 3.45-3.42 (m, 1H), 3.38-3.33 (m, 1H), 3.27-2.90 (m, 6H), 2.77-2.62 (m, 2H), 1.18 (s, 9H).

Figure 2:
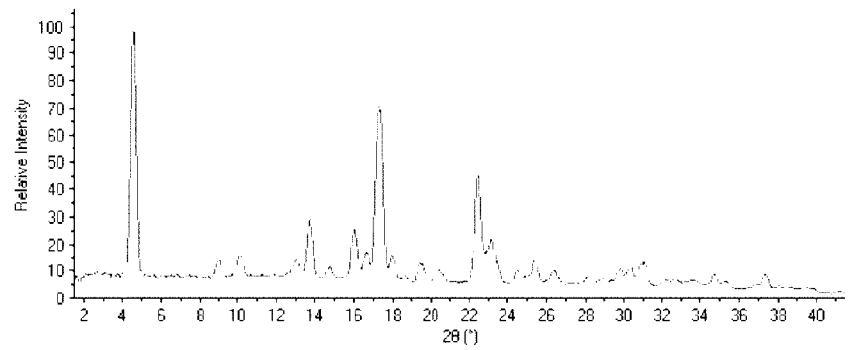
FIG. 2 shows the XRPD pattern of (S)-6-chloro-7-(1,1-dimethylethyl)-2-trifluoromethyl-2H-1-benzopyran-3-carboxylic acid meglumine salt.

XRPD (FIG. 2): Main peaks at 2-Theta 4.6, 8.9, 10.1, 13.8, 16.0, 16.7, 17.3, 18.0, 19.5, 22.4 and 23.2 (°). Each peak has a margin of error of +/−0.2 (°).

Figure 3:
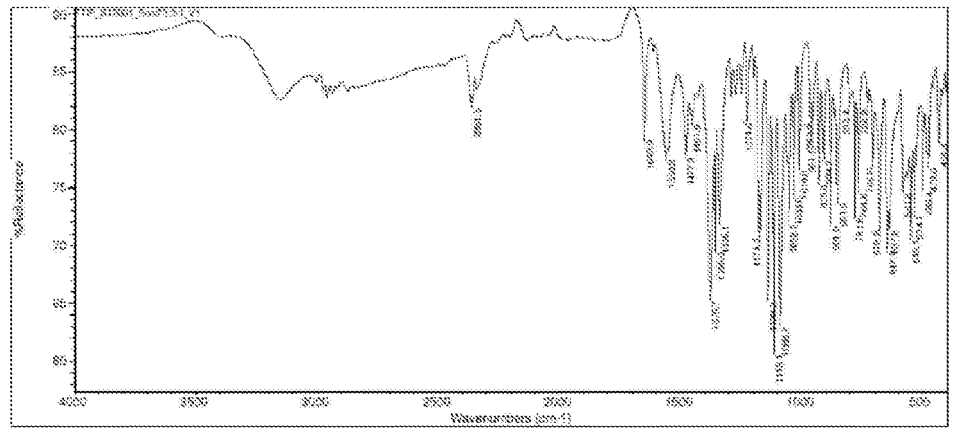
FIG. 3 shows the FTIR spectrum of (S)-6-chloro-7-(1,1-dimethylethyl)-2-trifluoromethyl-2H-1-benzopyran-3-carboxylic acid meglumine salt.

FTIR (FIG. 3): 534, 549, 638, 647, 678, 765, 782, 852, 881, 929, 1033, 1053, 1089, 1115, 1139, 1174, 1338, 1356, 1377, 1477, 1560, 1649, and 2362 cm$^{-1}$. Each peak has a margin of error of +/−2 cm$^{-1}$.

m.p. (DSC Peak): 186° C.

HPLC analysis showed that both chemical and chiral purities were 99.9%.

DVS analysis showed the maximum water uptake was 2.0% at 95% RH. The XRPD pattern of the sample after DVS measurement was not changed.

The meglumine salt was also obtained using ethanol instead of isopropanol.

Example 2

Variable temperature XRPD (VT-XRPD) measurements of the meglumine salt were performed under the temperature of 25° C. to 160° C. (heating) and thereafter decreased to 25° C. (cooling). The meglumine salt remained unchanged throughout the heating-cooling cycle.

Example 3

Variable humidity XRPD (VH-XRPD) measurements of the meglumine salt were performed under the humidity of 60 to 80% RH (1st sorption), 80 to 10% RH (desorption) and 10 to 50% (2nd sorption). The meglumine salt remained unchanged throughout the sorption-desorption-sorption cycle.

Example 4

The slurry experiments of the meglumine salt were performed; the materials (15-30 mg) were weighed into 1.8 ml vials, charged with a stirring bar and the solvent (ethanol, ethyl acetate and n-heptane) and the slurries were placed at 25° C. under stirring. After two weeks, the slurries were subject to centrifugation and the liquid was removed with a pipette. The solids were sampled "wet" for XRPD. Subsequently the remaining solids dried under 200 mbar at room temperature for 5 days and all solids were analyzed as "dry" by XRPD.

All "wet" and "dry" solids of the meglumine salt were physically stable after 2 weeks in all three solvents.

Example 5

The API (753 mg) and potassium hydroxide (161 mg) were weighed into 40 ml vial. The material was dissolved after addition of water/isopropanol 50/50 (V/V) mixture (5 ml). The solution was left stirring at ambient temperature for 1 hour before placing under vacuum. The solvents were slowly evaporated. The solids were analyzed by XRPD. Subsequently, the obtained solids were made wet with 200 µl of water, stirred for 15 minutes and placed under full vacuum at ambient conditions to provide the potassium salt (822 mg, 92% yield).

Figure 4:
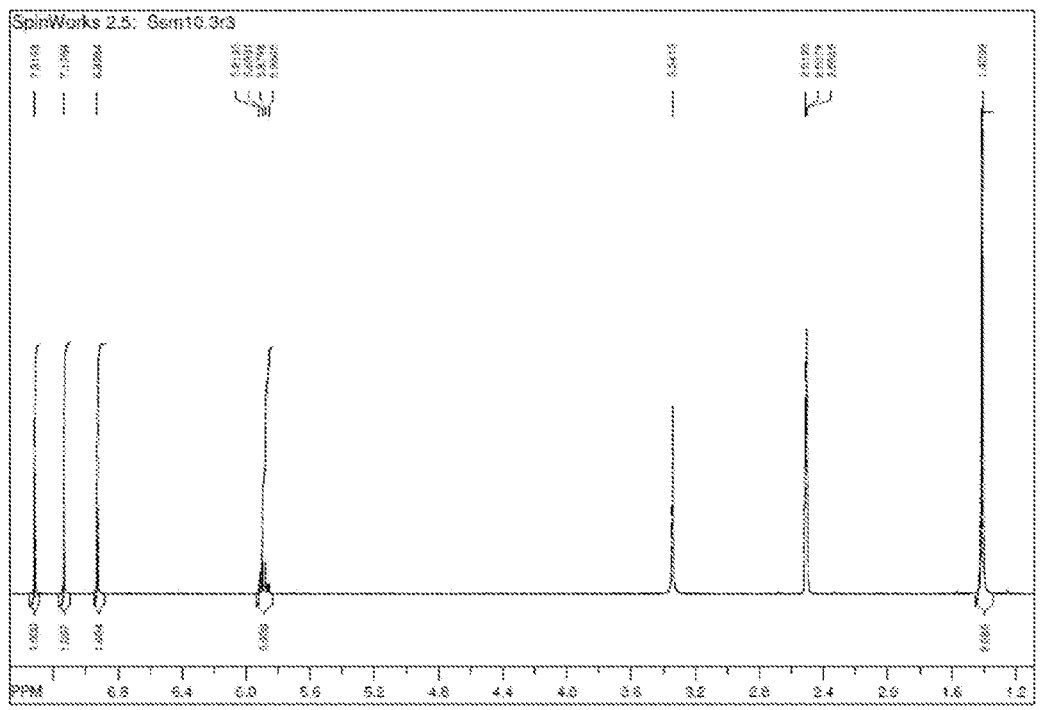
FIG. 4 shows the NMR spectrum of (S)-6-chloro-7-(1,1-dimethylethyl)-2-trifluoromethyl-2H-1-benzopyran-3-carboxylic acid potassium salt.

NMR (FIG. 4): $^1$H-NMR (DMSO-$d_5$) delta: 7.32 (s, 1H), 7.14 (s, 1H), 6.93 (s, 1H), 5.89 (q, J=7.7 Hz, 1H), 1.41 (s, 9H).

Figure 5:
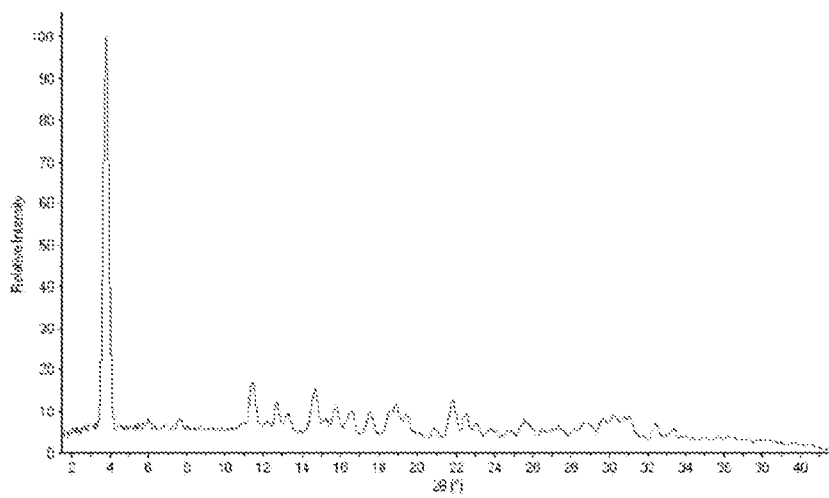
FIG. 5 shows the XRPD pattern of (S)-6-chloro-7-(1,1-dimethylethyl)-2-trifluoromethyl-2H-1-benzopyran-3-carboxylic acid potassium salt.

XRPD (FIG. 5). Main peaks at 2-Theta 3.8, 11.4, 12.7, 14.7, 15.8, 16.5, 17.4, 18.9, 19.5 and 21.8 (°). Each peak has a margin of error of +/−0.2 (°).

Figure 6:
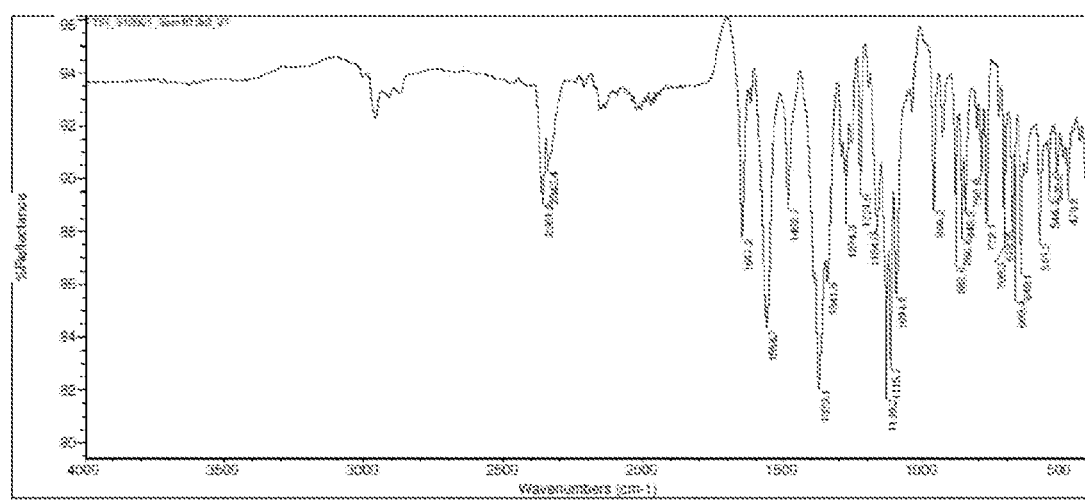
FIG. 6 shows FITR spectrum of (S)-6-chloro-7-(1,1-dimethylethyl)-2-trifluoromethyl-2H-1-benzopyran-3-carboxylic acid potassium salt.

FTIR (FIG. 6): 480, 548, 581, 648, 669, 679, 708, 772, 848, 861, 882, 960, 1095, 1116, 1130, 1164, 1225, 1275, 1373, 1483, 1559, 1647, 2342, and 2361 cm$^{-1}$. Each peak has a margin of error of +/−2 cm$^{-1}$.

DSC Peak: 117° C.

HPLC analysis showed that both chemical and chiral purities were very high (≥99.9%).

The obtained salt was confirmed monohydrate according to Karl-Fischer method.

Example 6

The solid-state stabilities were assessed as follows: HPLC vials, containing approximately 5 mg of material, were placed in the climate chamber at 40° C. and 75% relative humidity. The samples were analyzed by XRPD and HPLC (both purity and chiral) at time points of 1, 2, 3 and 4 weeks. For each week a separate vial was prepared.

The meglumine salt remained physically and chemically stable within this period. Its enantiomeric purity remained ?_99.9%.

Both chemical and enantiomeric purities of the potassium salt were very high (≥99.9%).

Example 7

Quantitative Solubility Assessment were performed on the free acid, the meglumine salt, and the potassium salt. The measurements were carried out in pH 6.8 phosphate buffer (0.05M) and water.

A standard 1.8 ml screw cap vial was charged with the material, each solvent (medium) and a magnetic stirring bar. The vials were subsequently closed and equilibrated at the ambient temperature for 24 h while stirring.

The liquid part was retrieved with a syringe and filtrated (0.5 micron filter); the isolated mother liquors were diluted to two dilutions selected according to the calibration curve. Quantities of the API in the diluted solutions were determined via HPLC analysis (DAD). The calibration curve was obtained from two independently prepared stock solutions of the API in 50% water/50% acetonitrile.

Figure 7:
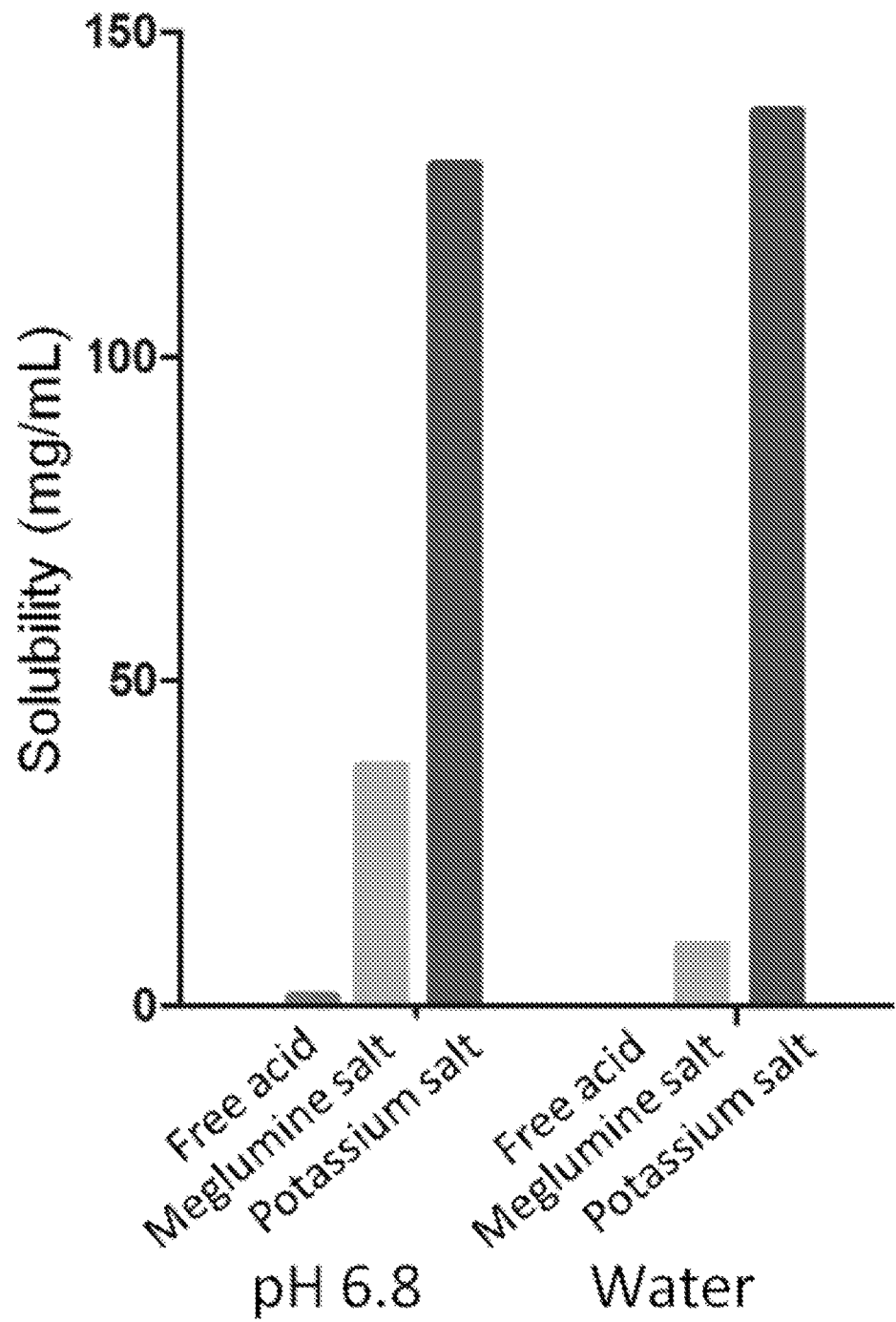
FIG. 7 shows the solubility of the salts.

The following FIG. 7 showed the solubility values. The solubility of the salts of the present invention are much higher than that of the free acid.

Example 8

Intrinsic dissolution experiments were performed on the free acid, the meglumine salt, and the potassium salt. The measurements were carried out in pH 6.8 (0.05 M) phosphate buffer and water.

The press used for tablet preparation for intrinsic dissolution rate measurements was a mini-IDR compression system (pION/Heath Scientific). Approximately 11 mg of material was pressed in the cylindrical hole of a passivated stainless steel die, to a uniform, flat surface, with an exposed area of 0.072 cm$^2$. The pressure applied was approximately 50 bar for 3-5 min. The sample die was inserted in a cylindrical Teflon rotating disk carrier containing an embedded magnetic stirring bar at its base. The die/stirrer assembly was placed in a flat bottomed glass vial, ready for dissolution analysis.

The dissolution rate was measured in 20 ml of solvent (medium) and the path length of the UV meter was 2 mm. Applied stirring speed during measurement was 100 rpm. Measurements were performed at 20° C.

In FIG. 8, the concentrations vs. time of all solids measured in the pH 6.8 buffer are shown.

The concentration of the free acid after one hour reached 27 µg/ml. The concentration increased linearly, within the time interval of the measurement.

The concentration of the meglumine salt increased linearly in the first 45 min and it reached a plateau at about 250 µg/ml. The plateau is attributed to the dissolution of the complete tablet whereby concentration remains unchanged.

The concentration of the potassium salt reached a value of 370 µg/ml, within 15 min (dissolution of complete tablet).

In FIG. 9, the concentrations vs. time of all solids measured in water are shown.

The dissolution of the free acid is very poor with concentration of about 1 µg/ml after one hour.

The concentration of the meglumine salt increased fast in the first 9 min reaching a value of about 210 µg/ml, and thereafter the dissolution rate decreased. The concentration reached finally a value of 250 µg/ml, within about 1 h 25 min. Thereafter no changes in concentration were observed. The plateau is attributed to the dissolution of the complete tablet whereby concentration remains unchanged.

The concentration of the potassium salt reached 400 μg/ml, within 5 min (complete tablet dissolved).

The meglumine salt and the potassium salt are much better than the free acid in the intrinsic dissolution rate. Especially, the potassium salt dissolved the fastest in all cases.

Example 9

API (2.0 g) and meglumine (1.17 g, 1.0 equiv.) were charged to a round-bottom flask equipped with a stir bar. MeOH (30 ml) was charged and the resulting mixture was heated to 50° C. using a heating mantle so that the mixture forms a clear solution. MTBE (30 ml) was added to this solution via a syringe, resulting in thick slurry. The slurry was cooled to room temperature (approximately 20° C.) and allowed to stir overnight at room temperature. The slurry was filtered and the 1st filtered solid was dried under vacuum at room temperature to provide the meglumine salt (2.443 g, 77% yield).

$^1$H-NMR (CD$_3$OD): delta: 7.38 (s, 1H), 7.22 (s, 1H), 7.01 (s, 1H), 5.82 (q, J=7.5 Hz, 1H), 4.06-4.00 (m, 1H), 3.83-3.81 (m, 1H), 3.80-3.75 (m, 1H), 3.70-3.62 (m, 3H), 3.16-3.14 (m, 2H), 3.27 (s, 3H), 1.46 (s, 9H).

XRPD: The X-ray powder diffraction pattern was identical with that of a product of example 1.

m.p. (DSC Peak): 187.1° C.
HPLC Area % (Chemical purity): ≥99.9%
HPLC Area % (Chiral purity): ≥99.9%

Example 10

API (2.0 g) was charged to a round-bottom flask equipped with a stir bar. 2-MeTHF (20.0 ml) was added so that the solid was dissolved. A solution of 2.0 M potassium hydroxide in MeOH (3.0 ml) was added to the 2-MeTHF solution and the resulting mixture was stirred for approximately 5 minutes. The solution was evaporated to dryness on a rotovap. Then, MTBE (40 ml) was added so that the dry matter was dissolved, and the solution was evaporated to dryness. Addition of MTBE and evaporating to dryness was repeated three times to ensure complete removal of MeOH. The foamy residue was dissolved in 2-MeTHF (8 ml) in a round-bottom flask and the solution was heated to 50° C. using a heated mantle. A total of 160 ml of n-heptane was then added in 5 portions as described below:

1. 10 ml of n-heptane was added as the first portion. At this point, approximately 5 mg of seed crystal of potassium salt was added to the solution. The seeds remained undissolved. It was observed that precipitation started to occur prior to seeding at the sides of the round bottom flask possibly due to solvent evaporation.

2. An additional 10 ml of n-heptane was added. Precipitation progressed rapidly and resulted in thick slurry.

3. A third portion of n-heptane (20 ml) was added so that the slurry can be stirred.

4. A fourth portion of n-heptane (80 ml) was added and cooling was initiated at the rate of 20° C./h to room temperature.

5. When the temperature of the slurry was reached at the ambient temperature, a fifth portion of n-heptane (40 ml) was added and stirred overnight at room temperature.

A sample was aliquoted from the slurry, filtered and analyzed by XRPD. XRPD of the sample indicated poor crystallinity and likely presence of some anhydrate form. Seed crystal of potassium salt (100.7 mg, 5 wt %; XRPD pattern identical with example 5) was added and the mixture was stirred overnight. A sample was aliquoted the next day and analyzed by XRPD. XRPD did not show improvement in crystallinity. It was hypothesized that formation of hydrate is being inhibited by lack of moisture for hydrate formation. Therefore 80 μL water (4.0 wt %) was added to the slurry and the mixture was stirred overnight. XRPD of an aliquot in the following day was consistent with an authentic sample. The reaction was filtered and dried under vacuum giving the potassium salt (2.322 g, 98.7%) as a white solid.

NMR: The $^1$H-NMR spectrum was identical with that of a product of example 5.

XRPD: The X-ray powder diffraction pattern was identical with that of a product of example 5.

m.p. (DSC Peak): 291.3° C.
HPLC Area % (Chemical purity): ≥99.9%
HPLC Area % (Chiral purity): ≥99.9%

Example 11

The salt formation was set up following the procedure described for EXAMPLE 10. API (2.0 g) was charged to a round-bottom flask equipped with a stir bar. 2-MeTHF (20.0 ml) was added to dissolve the solid. A solution of 2.0 M potassium hydroxide in MeOH (3.0 ml) was added and the resulting mixture was stirred for approximately 5 minutes. Solvent was evaporated to dryness on a rotovap. MTBE (40 ml) was added and rotovaped to dryness. Addition of MTBE and rotovaping to dryness was repeated three times to ensure complete removal of MeOH. The foamy residue was dissolved in 2-MeTHF (8 ml) in a round-bottom flask and the solution was heated to 50° C. using a heated mantle. A total of 160 ml of n-heptane was then added in 5 portions as described below:

1. 5.0 ml n-heptane was added as the first portion. The solution was seeded at this point with a crystal of potassium salt. The seed crystal was visually dissolved. No precipitation was observed.

2. After 5 min, another 5.0 ml of n-heptane was added. The solution turned cloudy.

3. Precipitation started to occur gradually. 5.0 ml portion of n-heptane was added after every 5 min till a total of 40 ml was introduced.

4. 80 ml of n-heptane was added in 20 ml portions over a period of 20 min. The slurry was cooled to room temperature.

5. 40 ml of n-heptane was added after the slurry was cooled to room temperature and allowed to stir overnight at room temperature.

A sample was aliquoted, filtered and analyzed by XRPD. XRPD of the sample was consistent with an authentic sample. The reaction was filtered and dried under vacuum giving the potassium salt (2.198 g, 97.4%) as a white solid.

NMR: The 1H-NMR spectrum was identical with that of a product of example 5.

XRPD: The X-ray powder diffraction pattern was identical with that of a product of example 5.

m.p. (DSC Peak): 291.4° C.
HPLC Area % (Chemical purity): 99.9%
HPLC Area % (Chiral purity): 99.9%

Example 12

In vivo pharmacokinetic study was carried out in Beagle dogs.

Method)

Male Beagle dogs were given single oral dose of the test articles by gelatin capsule formulation at a dose of 5 mg/kg. The actual weight of the test articles in the gelatin capsule to be administered to each animal was calculated based on the body weight measured just before the administration.

Following dosing, blood was collected from the external jugular vein of animals at 0, 0.25, 0.5, 1, 2, 4, 6, 8, 12, 24, 48, 72, 96, 120, 144, 168, 216, 216, 288, and 360 hour after administration. Approximately 1 mL of blood will be collected into tubes containing heparin-Na.

On the day of administration, food was given to the animals after 6-hour blood sampling.

The drug concentrations in dog plasma were determined with the validated bioanalytical assay procedures. PK parameters were determined with non-compartmental analysis.

(Result)

Figure 10:
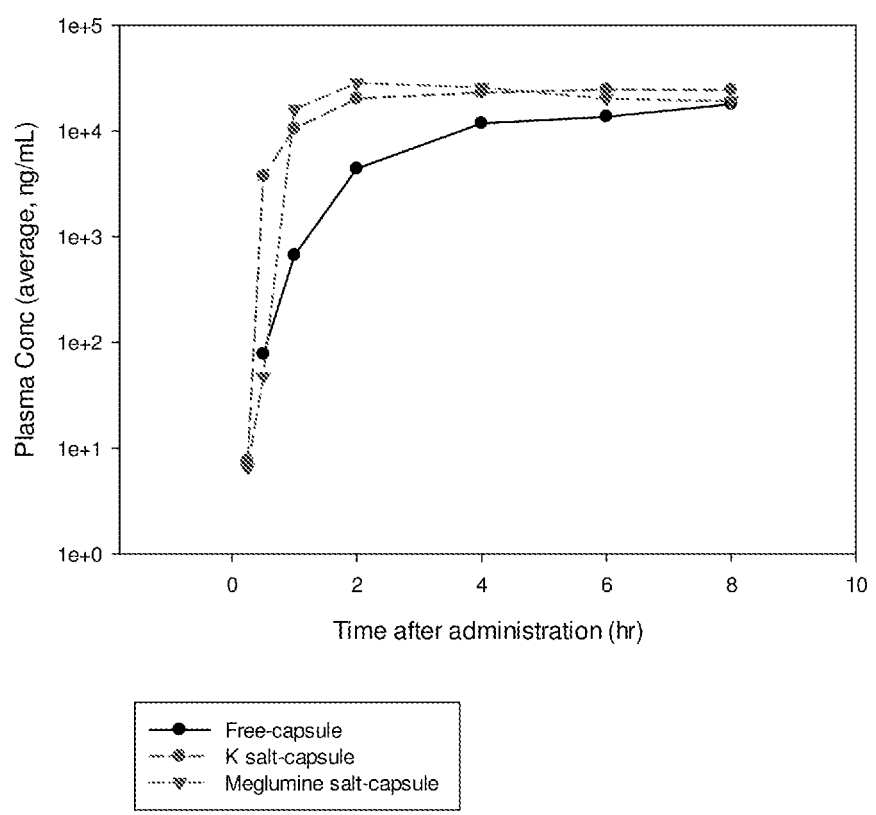
FIG. 10 shows the time-course of mean plasma concentrations after oral administration of capsule formulations of API (free acid), Potassium-salt and Meglumine-salt to male Beagle dogs.

FIG. 10 shows the time-course of mean plasma concentrations after oral administration of capsule formulations of API (free acid), Potassium-salt and Meglumine-salt to male Beagle dogs. Plasma concentration rapidly increased after oral dose of Potassium-salt and Meglumine-salt in comparison with API.

As shown in Table 1, the $C_{max}$ and $AUC_{0-24h}$ values were increased after administration of Potassium-salt and Meglumine-salt in comparison with API.

The unique characteristics of Potassium-salt and Meglumine-salt were identified in dog-pharmacokinetic studies.

TABLE 1

|  | $C_{max}$ (ng/mL) | $AUC_{0-24h}$ (ng · hr/mL) |
| --- | --- | --- |
| Free acid | 19,700 | 287,000 |
| K-salt | 28,200 | 436,000 |
| Meglumine-salt | 28,200 | 381,000 |

The invention claimed is:

1. A salt of (S)-6-chloro-7-(1,1-dimethylethyl)-2-trifluoromethyl-2H-1-benzopyran-3-carboxylic acid; wherein the salt is selected from the group consisting of a potassium salt and a meglumine salt.

2. The salt according to claim 1, wherein the potassium salt is a hydrate.

3. The salt according to claim 1, wherein the potassium salt is a monohydrate.

4. A crystal form of a meglumine salt of (S)-6-chloro-7-(1,1-dimethylethyl)-2-trifluoromethyl-2H-1-benzopyran-3-carboxylic acid, which is characterized by a powder X-ray diffraction pattern (PXRD) obtained by irradiation with Cu-Kα radiation having main peaks at 2-Theta of 4.6, 8.9, 10.1, 13.8, 16.0, 16.7, 17.3, 18.0, 19.5, 22.4 and 23.2)(°) and each peak has a margin of error of +/−0.2)(°).

5. A crystal form of a potassium salt of (S)-6-chloro-7-(1,1-dimethylethyl)-2-trifluoromethyl-2H-1-benzopyran-3-carboxylic acid, which is characterized by a powder X-ray diffraction pattern (PXRD) obtained by irradiation with Cu-Kα radiation having main peaks at 2-Theta of 3.8, 11.4, 12.7, 14.7, 15.8, 16.5, 17.4, 18.9, 19.5 and 21.8)(°) and each peak has a margin of error of +/−0.2)(°).

6. A pharmaceutical composition comprising a pharmaceutically acceptable carrier and a pharmaceutically effective amount of the salt according to claim 1.

7. A process for preparing a pharmaceutical composition, which comprises combining the salt according to claim 1 and a pharmaceutically acceptable carrier.

8. The process for preparing the pharmaceutical composition according to claim 7,
further comprising subjecting the combined salt and carrier to grinding, milling, sieving, blending, drying, or granulating.

9. The process according to claim 7, wherein the process further comprises compressing the pharmaceutical composition into a solid dosage form.

10. A process for preparing the potassium salt according to claim 1, wherein the process comprises:
combining (S)-6-chloro-7-(1,1-dimethylethyl)-2-trifluoromethyl-2H-1-b enzopyran-3-carboxylic acid in free acid form with an aqueous solvent comprising potassium to obtain a mixture, and
adding a suitable solvent to the mixture, and
removing the aqueous solvent by an azeotropic condition to obtain the potassium salt,
wherein the mixture comprises less than 1.5 molar equivalent of water content against the (S)-6-chloro-7-(1,1-dimethylethyl)-2-trifluoromethyl-2H-1-benzopyran-3-carboxylic acid in free acid form.

11. The process according to claim 10, wherein the water content is selected from the group consisting of
a) 1 to 1.5,
b) 1 to 1.2,
c) 1 to 1.1 and
d) 1 to 1.05.

* * * * *